United States Patent [19]

Caillot et al.

[11] Patent Number: 4,537,190

[45] Date of Patent: Aug. 27, 1985

[54] PROCESS AND DEVICE FOR CONTROLLING ARTIFICIAL RESPIRATION

[75] Inventors: Luc Caillot, Paris; Claude Chopin, Attiches, both of France

[73] Assignee: SYNTHELABO, Paris, France

[21] Appl. No.: 447,584

[22] Filed: Dec. 7, 1982

[30] Foreign Application Priority Data

Dec. 11, 1981 [FR] France .............................. 81 23193

[51] Int. Cl.³ .............................................. A61M 16/00
[52] U.S. Cl. .............................. 128/204.22; 128/205.23
[58] Field of Search ................... 128/204.21, 204.22, 128/204.23, 205.11, 205.23

[56] References Cited

U.S. PATENT DOCUMENTS

| | | | |
|---|---|---|---|
| 3,693,653 | 9/1972 | Cramer et al. ................. | 128/205.11 |
| 3,951,137 | 4/1976 | Conkle et al. ................. | 128/204.23 |
| 4,112,938 | 9/1978 | Peretin ............................ | 128/204.23 |
| 4,121,578 | 10/1978 | Torzala ............................ | 128/204.23 |
| 4,188,946 | 2/1980 | Watson et al. ................. | 128/204.22 |

FOREIGN PATENT DOCUMENTS 459242 4/1975 U.S.S.R. ......................... 128/204.22

OTHER PUBLICATIONS

Mitamura et al., "An Optimally Controlled Respirator", IEEE Transactions on Bio-Medical Engr., vol. BME-18, No. 5, Sep. 1971.

*Primary Examiner*—Henry J. Recla
*Attorney, Agent, or Firm*—Sughrue, Mion, Zinn, Macpeak, and Seas

[57] ABSTRACT

The stopping or starting of the respirator (1) is controlled by a module (11) receiving, from a capnograph (8), an electric signal representing the $CO_2$ content of the gas passing through a $CO_2$ analysis cell (6) fixed to the exit of the intubation tube, inserted after tracheotomy, of a patient under assisted respiration. It is the $CO_2$ content which determines the starting or stopping of the assistance by the respirator.

7 Claims, 6 Drawing Figures

PROCESS AND DEVICE FOR CONTROLLING ARTIFICIAL RESPIRATION

The present invention relates to an improvement to artificial respirators or ventilators and more particularly to new equipment intended for facilitating the withdrawal of patients from assisted ventilation and the surveillance of the spontaneous ventilation modes (SV-CPAP-IMV). It also relates to a new procedure for controlling artificial respiration.

Systems are currently available which permit mandatory ventilation during the withdrawal of patients from assisted ventilation which they are receiving for an episode of acute respiratory insufficiency. Amongst these systems, the following are known in particular:

spontaneous ventilation with the use of the respirator, which delivers to the patient a gaseous mixture of constant oxygen concentration, temperature and moisture content. The spirometry can be monitored. In the event of apnea (absence of respiration), the ventilator resumes control after a constant delay. The addition of a residual positive pressure is possible; it is commonly called CPAP: Continuous Positive Airway Pressure.

the use of the Trigger, or self-triggered ventilation, the patient controlling the frequency of operation of the respirator.

intermittent mandatory ventilation, which permits partial assisted ventilation at a rate of n spontaneous cycles per controlled cycle (2/1, 3/1, 4/1, and so on). This system can operate in a synchronous or non-synchronous mode. It is commonly called IMV.

determined forced ventilation, in which a base spirometry is defined which the patient must exceed under spontaneous ventilation. If the spontaneous spirometry of the patient is below a limit which can be fixed by the doctor, the ventilator resumes control. This system is usually called MMV: Minute Mandatory Ventilation.

None of these systems is fully satisfactory. In fact, none of them takes account of the efficacy of the spontaneous ventilation of the patient.

According to the present invention, the ventilation of a patient is controlled by the carbon dioxide content of the gas exhaled by the patient. According to the present invention, a cell for analysing the $CO_2$ content of the exhaled gas, a capnograph, this being an apparatus which receives the $CO_2$ content from the cell and converts it to an analog electrical signal, and a mandatory ventilation module controlled by the $CO_2$ content, this being an apparatus which receives the analog signal from the capnograph and controls the running of an artificial respirator, are added to the respirator.

The cell and the capnograph are known apparatuses available commercially. The module is new and constitutes an important characteristic of the present invention.

The system according to the invention, which thus includes a process and a device, takes account of the respiratory efficacy of the patient and permits the withdrawal under maximum safety conditions for the minimum intervention by the nursing staff.

Other characteristics of the invention will become apparent in the course of the description which now follows and is given by way of a non-limiting example with reference to the attached drawing, and which will provide a clear understanding of how the invention can be carried out.

In the remainder of the description, the use of bistable elements will be described; these can assume two states: a low state, or zero, and a high state, or one. For the purpose of simplification, the expressions zero and one will be used without assigning a limiting character thereto.

Figure 1:
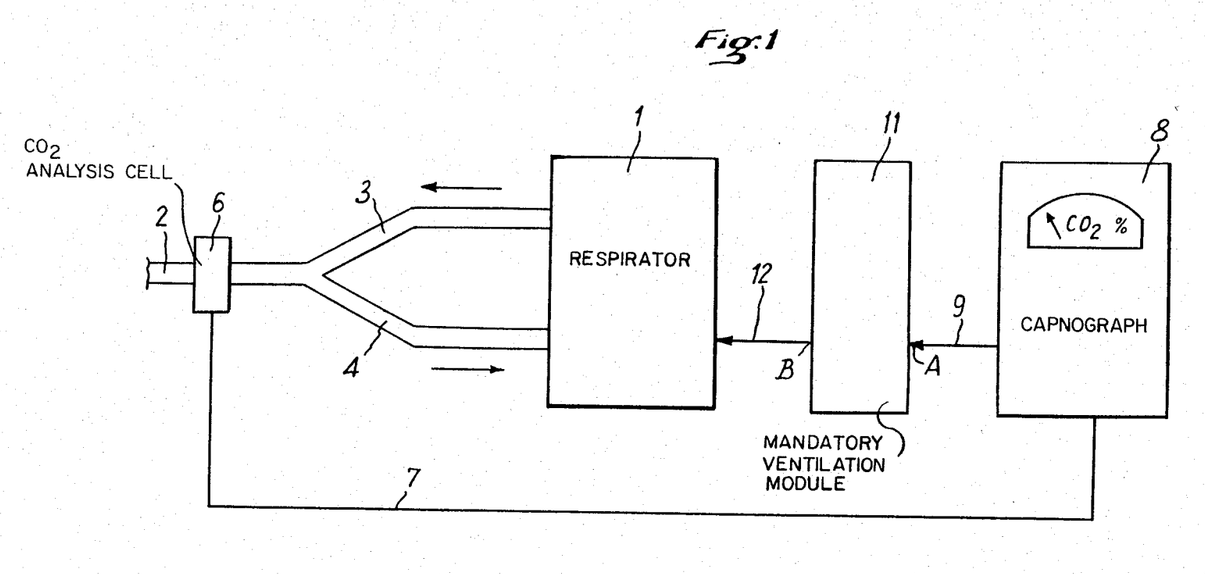
FIG. 1 is a general diagram of the device according to the invention.

As shown in FIG. 1, a device according to the invention includes an artificial ventilator or respirator 1, which can be of any type, connected to a patient by means of an intubation tube, inserted after tracheotomy, or less frequently by means of a mask, 2, supplied by an inhalation line 3 and an exhalation line 4. A $CO_2$ analysis cell 6, connected by a line 7 to a capnograph 8, is placed in the dead space of the equipment (the part of the circuit swept alternately by the inhaled gas and by the exhaled gas). The capnograph is connected by a line 9 to the input A of the mandatory ventilation module 11 ($M.V.CO_2$), the output B of which is connected by a line 12 to the ventilator 1.

The apparatus can be fitted to all modern ventilators possessing a spontaneous operating mode. The capnogram is collected in the dead space of the equipment (FIG. 1). The maximum concentration (at the end of each exhalation) of $CO_2$ exhaled by the patient ($FCO_{2ET}$; ET=End Tidal or end of cycle) is the value constantly monitored.

Figure 2:
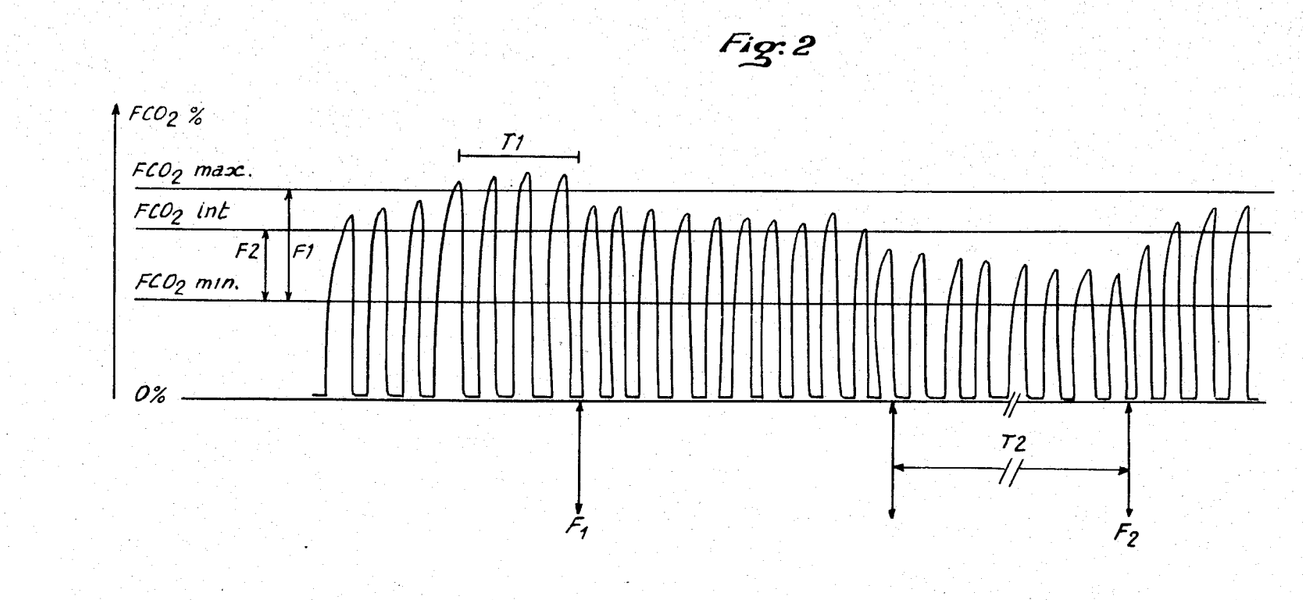
FIG. 2 is a representation of an analog signal delivered by the capnograph.

FIG. 2 shows the analog output signal from the capnograph. During inhalation, the $CO_2$ concentration is zero. Each tooth of the curve represents one period of exhalation: the concentration is at its maximum at the end of each exhalation.

The doctor determines two monitoring ranges; the first is between a minimum and maximum threshold: this is range no. 1 (F1)—FIG. 2—called the spontaneous ventilation range; the second is between the same minimum threshold and an intermediate threshold below the maximum threshold: this is range no. 2 (F2), called the controlled ventilation range.

The maximum threshold ($FCO_2max$) is calculated as the difference between $PCO_{2ET}$ (partial pressure of the $CO_2$ exhaled at the end of exhalation) and the partial pressure of $CO_2$ in the arterial blood ($PaCO_2$). This gradient is a characteristic of the patient at the moment of withdrawal. (The withdrawal is the period of removal of the ventilator as from the moment when the patient has an acceptable autonomous respiration.) Its determination requires analysis of the gases in the arterial blood.

$$PCO_{2ET} = FCO_{2ET} \times (PB - PBH_2O) \text{ or}$$
$$FCO_{2ET} = PCO_{2ET}/(PB - PBH_2O)$$

$$PCO_{2ET} = PaCO_2 - (PaCO_2 - PCO_{2ET})$$

where PB is the barometric pressure and $PBH_2O$ is the partial pressure of water vapour, $FCO_{2ET}$ the $CO_2$ concentration of the gas exhaled at the end of exhalation, $PCO_{2ET}$ the partial pressure of $CO_2$ in the gas exhaled at the end of exhalation, and $PaCO_2$ the partial pressure of $CO_2$ in the blood.

For example, if it is desired that the $PaCO_2$ of the patient should not exceed 45 mm Hg, for a gradient of 12 mm Hg:

$PCO_{2ET} = 33$ mm Hg $= 45 - 12$ $FCO_{2ET} = 33/730$ for PB $= 760$ and $PBH_2O = 47$ at 37° C.

$FCO_{2ET} = 4.52\%$

The maximum threshold $FCO_2$max will be fixed at 4.5%.

The minimum threshold ($FCO_2$min) is always above 1% of $CO_2$. It enables the ventilator to resume control in the event of apnea, acute cardio-circulatory failure, cardiac arrest or very substantial tachycardia.

The intermediate threshold ($FCO_2$int) is always between $FCO_2$max and $FCO_2$min. In the controlled ventilation mode, $FCO_{2ET}$ must always be between $FCO_2$min and $FCO_2$int.

When the system is started, the patient is under controlled ventilation and the values of $FCO_2$min and $FCO_2$int are determined; the patient is then placed under spontaneous ventilation and $FCO_2$max is determined.

Whilst the patient has satisfactory ventilation with $FCO_2\text{min} < FCO_{2ET} < FCO_2\text{max}$ he remains under spontaneous ventilation. As soon as he exceeds the thresholds (in practice, he most frequently exceeds the maximum threshold, $FCO_2$max), the apparatus automatically engages the "controlled ventilation" mode if the excess is constant and its duration is longer than a period whose variable duration can be fixed, for example, at 15 or 20 seconds (time delay T1). Under controlled ventilation, $FCO_{2ET}$ decreases rapidly and must again be situated between $FCO_2$min and $FCO_2$int.

$FCO_2\text{min} < FCO_{2ET} < FCO_2\text{int}$

If $FCO_{2ET}$ in fact remains between these two thresholds for a period which can be fixed, for example, at 5 minutes (time delay T2), the apparatus then stops the respirator and indicates the spontaneous ventilation mode of the patient. The duration of T1 and T2 can be adjusted inside the apparatus. Between the end of T1 and the end of T2 (FIG. 2), the patient's ventilation is controlled; outside this period, it is spontaneous.

Any absence of a cycle, or apnea during inhalation or exhalation, automatically starts the respirator and initiates the controlled ventilation mode after a time equal to T1.

Any malfunction of the capnograph, or any absence of supply to the system, also initiates the controlled mode, as does the stopping of the apparatus spontaneously or as a result of a supply fault.

Figure 3:
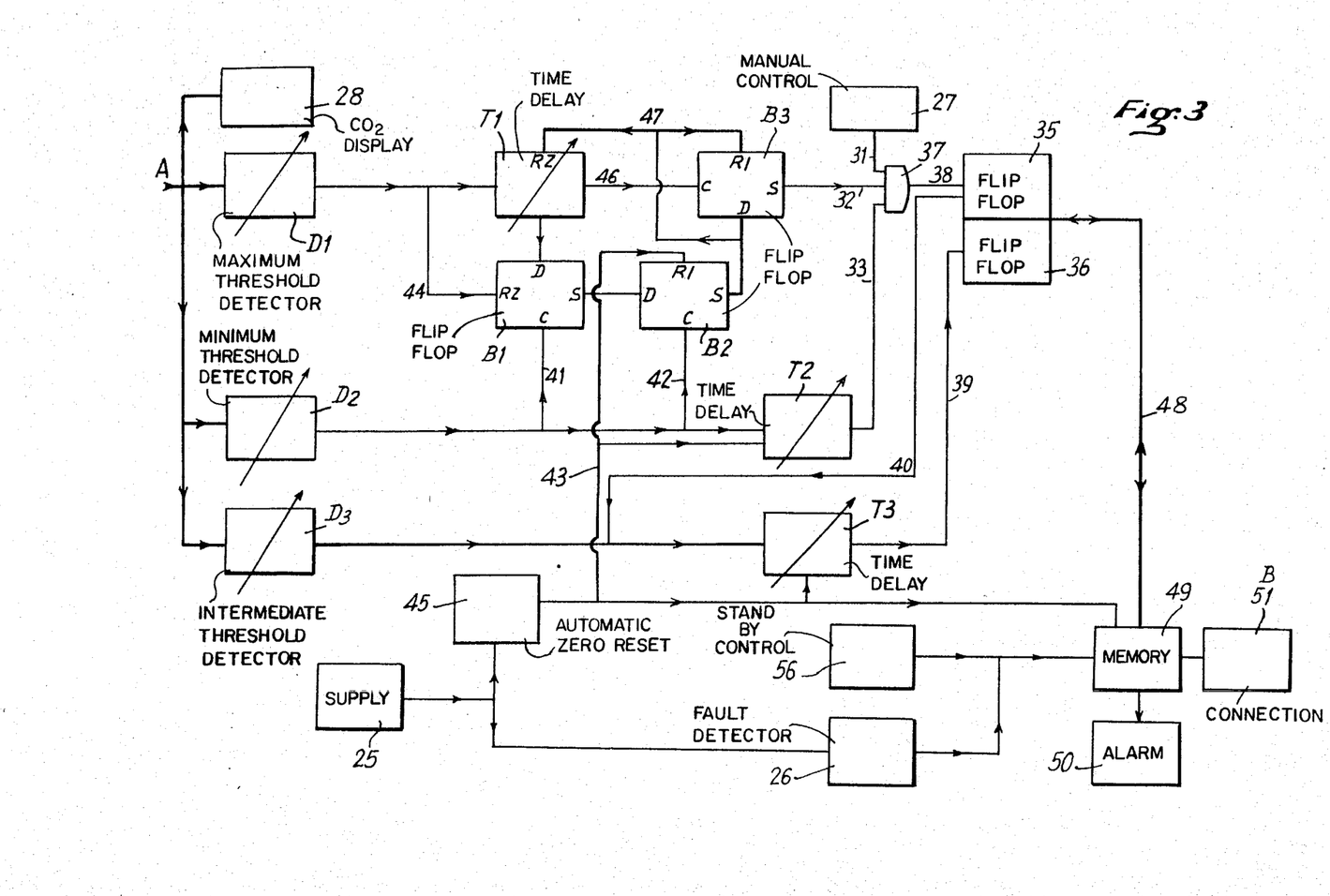
FIG. 3 is a block diagram of the module according to the invention.

The apparatus possesses a stand-by control 56, FIG. 3, which suspends the operation of the apparatus during the aspiration and care of the patient. The controlled ventilation mode has now been adopted. Cancellation of the "stand-by" position causes the system to revert to the mode in which it was operating before suspension.

FIG. 3 shows a simplified diagram of the module 11 of FIG. 1. The $CO_2$ signal coming from the capnograph 8 is delivered at the point A. By way of a convenient example, a concentration of 1% of $CO_2$ can be represented by a voltage of 1 volt. The module includes a supply 25 with a mains fault detector 26, and a manual control 27. A display 28 for the $CO_2$ content can advantageously be provided. The module includes three threshold detectors: a maximum threshold detector D1, a minimum threshold detector D2 and an intermediate threshold detector D3. In one embodiment of the invention, these detectors can be flip-flops which assume, at their outputs, the zero state when the input voltage is higher than the chosen voltage, and the one state when the input voltage is lower. The output B of the module is connected to the respirator through the connection 51, which is linked via the memory 49 (storage of the state of the respirator) to the control flip-flops 35,36: 35 for starting the respirator and 36 for stopping the respirator. Only the zero states cause the position of the flip-flops 35,36 to change.

The detectors D1, D2, D3 are each connected to a time delay T1, T2, T3. T1 is connected via a flip-flop B3 to the input 32 of an AND gate 37, the output 38 of which is connected to the start control 35. T2 is connected to the input 33 of the gate 37 and T3 is connected by the line 39 to the stop control 36.

The manual control 27 has its output connected to the input 31 of the gate 37. Manual control 27 is a two position manual device, such as a switch, which outputs a voltage corresponding to the aforementioned zero state in one position, and a voltage corresponding to the one state in the other position. If the three inputs 31, 32, 33 of the gate 37 are in the one state, the output 38 is in the one state, and this does not actuate the start control. If one of the inputs 31, 32, 33 is in the zero state, the output 38 is in the zero state, and this triggers the control 35 for starting the respirator. (Thus, if manual control 27 is operated to the position which provides a zero state on input 31, then the respirator stays on, regardless of the states of inputs 32 and 33, until control 27 is switched to its other position). When D1 changes over to the zero state ($FCO_2$max exceeded), T1 assumes the one state for (for example) 15 seconds. When D2 changes over to the zero state ($FCO_2$min exceeded), T2 assumes the one state for 15 seconds. If D2 remains in the one state, that is to say if $FCO_2$min is not reached for 15 seconds, T2 changes over to the zero state, and this triggers the start control (as soon as one of the inputs 31, 32, 33 is in the zero state), which triggers the sound alarm 50 via the memory 49. Through the line 40, the starting of the respirator triggers a pulse, which brings T3 to the one state for a sequence of 5 minutes (for example). The zero state of D3 ($FCO_2$int exceeded) keeps T3 each time in the one state for 5 minutes. If, for 5 minutes, T3 receives nothing from D3 ($FCO_2$int not exceeded, D3 remains in the one state), T3 changes over to the zero state, and this actuates the control 36 for stopping the respirator. Two flip-flops B1 and B2 are connected as shown. D1 is connected to the zero reset of B1 by the line 44, and T1 is connected to the input D of B1, the control C of which is connected by the line 41 to the output of D2. The output S of B1 is connected to the input D of B2, the control C of which is also connected to the output of D2, by the line 42. The one reset of B2 is connected by the line 43 to the automatic zero reset 45. The output S of B2 is connected to the input D of B3, the control C of which is connected by the line 46 to T1. The one reset of B3 is connected by the line 47 to the output S of B2, the line 47 also being connected to the zero reset of T1. The output S of B3 is connected to the input 32 of the gate 37. The flip-flops are set in the following way. For B1, a zero state of D2, via the line 41, passes the state of D on to S. For B2, a one state of D2, via the line 42, passes the state of D on to S. For B3, T1 sends a pulse to the control C at the end of the 15 second time delay period of T1. This pulse passes the state of D on to S.

The module operates in the following way.

When the apparatus is switched on, the automatic zero reset system sends a pulse to:

the one reset of the flip-flop B2, the output of which assumes the one state; this output controls the one reset of the flip-flop B3 and the zero reset of the time delay T1; the flip-flop B3 therefore assumes the one state at its output and T1 the zero state.

the input of the time delay T2, which assumes the one state at its output for 15 seconds.

the zero reset of the time delay T3, which assumes the zero state at its output.

the zero reset of the memory of the stand-by 46. Therefore, when the apparatus is switched on:

B3=1
T2=1
T3=0

As it is only the zero states which cause a change in position of the flip-flop for starting or stopping the respirator, the latter is initially off (T3=0).

If, after 15 seconds T2 has not received a pulse at its input coming from D2, it changes over to the zero state and the respirator starts to operate; as soon as the respirator starts, T3 receives a pulse and delays for a time set at, for example, 5 minutes.

If, after 5 minutes T3 has not received another pulse coming from D3 or from a possible second command for starting the respirator, the output of T3 then changes over to zero and the respirator is switched off.

The maximum detection proceeds as follows. At the moment when $FCO_2max$ is exceeded, D1 assumes the zero state, T1 changes over to one for 15 seconds and B1 is set to zero via the line 44. At the end of the exhalation, the following period of inhalation begins; $FCO_2=0$ and the three detectors therefore assume the one state. The one state of D2 is applied via the lines 41 and 42 to the inputs C of B1 and B2. This has no effect on B1, which is only sensitive to a zero state, but B2 is sensitive to the one state. As the output S of B1 is in the zero state, which is applied to the input D of B2, this state is transmitted to the output S of B2 by the changeover of D2 to the one state. When $FCO_2$ increases again due to the following exhalation, D2 assumes the zero state again, which causes the output S of B1 to assume the state of T1, that is to say, one.

Two cases can arise:

(1) The threshold of D1 is crossed again: B1 is reset to zero, $FCO_2$ then drops below the threshold of D2 again, and the output S of B2 assumes the state of B1, which it was already in, that is to say zero. This zero state is applied to the input D of B3, but is not transmitted to the output, which remains in the one state. Therefore, each time $FCO_2$ crosses the maximum threshold, minimum threshold, maximum threshold and so on, the operation repeats itself throughout the time delay of T1. T2 is in the one state, as is also the manual control in the absence of actuation, the three inputs 31, 32, 33 of the flip-flop 37 being in the one state; the flip-flop does not trigger the control 35 for starting the respirator. At the moment when T1 returns to zero, it sends a pulse to the control C of B3, which causes the output S of B3 to change over to the state of D, that is to say the state S of B2, which remains at zero. The changeover of the output S of B3 to the zero state orders the respirator to start.

(2) The threshold of D1 is not crossed again during the time delay of T1, but the threshold of D2 is crossed. B1 is not reset to zero; B2 then assumes the one state when D2 assumes the one state, which, via the line 47, sets the output of B3 to the one state and resets T1 to zero. Nothing happens and the respirator remains off.

By way of a summary, if D1 is crossed between the top of the range and the bottom of the range of D2, B2 remains in the zero state and the respirator starts up after the time T1. However, if D2 is crossed at the top of the range and then at the bottom of the range, without D1 having been exceeded, B2 changes over to the one state when D2 is crossed at the bottom of the range. If B2 is in the one state at the end of T1, the respirator is not switched on.

In the event of a power failure or of the selection of stand-by by the control 56, the state of the respirator is stored in 49 and is restored when the power returns or when the stand-by button is released.

Figure 4:
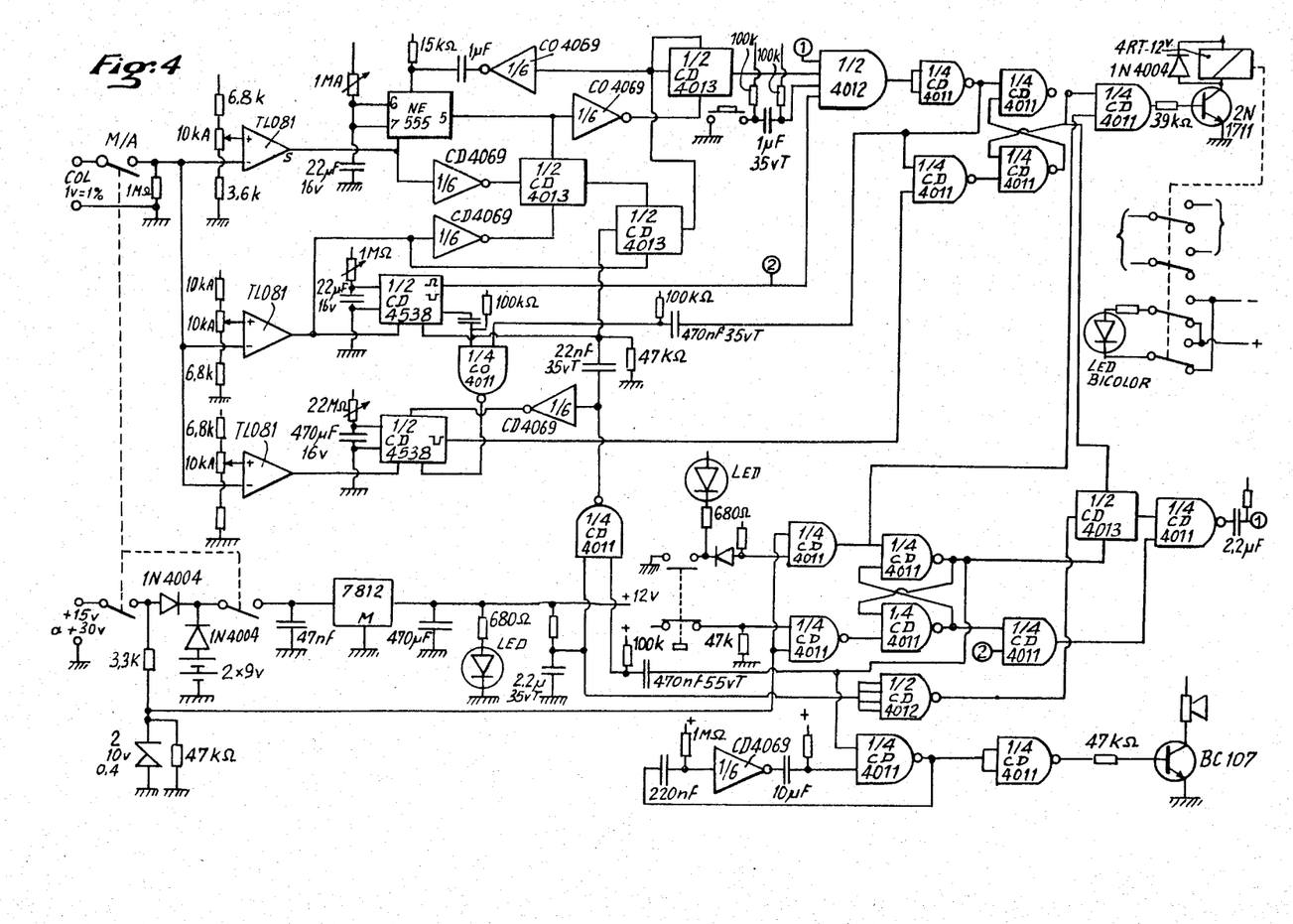
FIG. 4 is a complete diagram indicating the components of the module of FIG. 3.

FIG. 4 shows a practical example of the circuit with the conventional signs and the values of the components. Those skilled in the art can thus produce the entire device of the invention. It is obvious that variants or equivalents are possible both in the detail of the circuit and in the choice of the components or their values.

Figure 5:
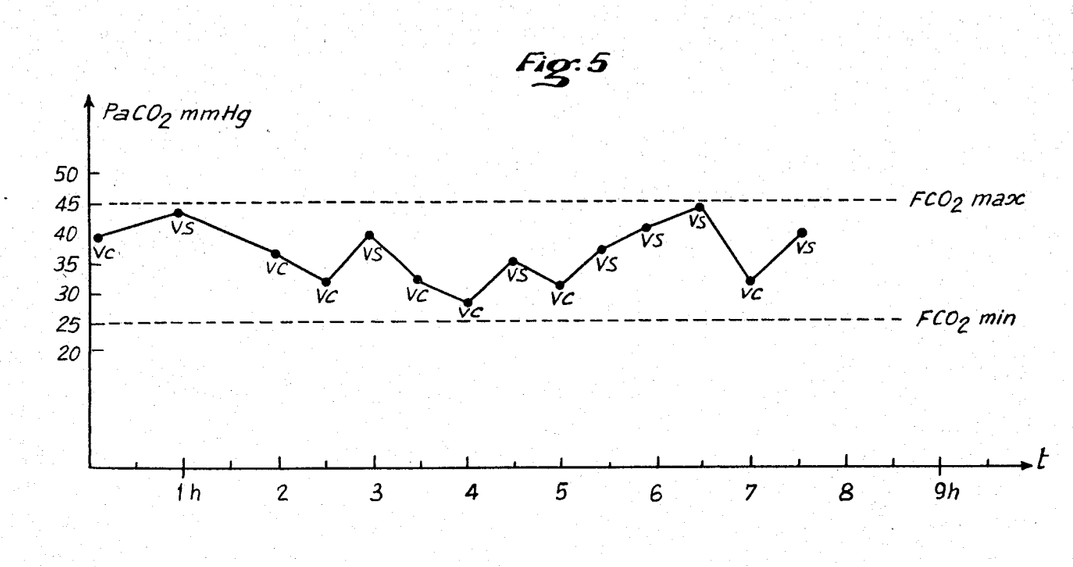
FIG. 5 is a representation of the change in the partial pressure of $CO_2$ in the blood ($PaCO_2$) in the course of one day, using the device according to the invention.

FIG. 5 shows the change in the $CO_2$ content of the gas exhaled in the course of one day. CV denotes controlled ventilation and SV denotes spontaneous ventilation. It is seen that the apparatus has the advantage of maintaining a constant $PaCO_2$ throughout the day.

FIG. 2 shows a sequence of spontaneous ventilation up to the end F1 of T1, controlled ventilation up to the end F2 of T2, and then spontaneous ventilation again.

The use of a microprocessor will permit earlier detection of the value of $FCO_{2ET}$ and averaging over three cycles, and will make it possible to fix the values of the various thresholds more precisely, to fix durations for T1 and T2 which can vary according to the patients, and, in particular, to envisage, between the controlled ventilation mode and the spontaneous mode, a gradual changeover to intermittent mandatory ventilation (IMV).

The changeover spontaneous ventilation→controlled ventilation will therefore take place as previously, but the changeover controlled ventilation→spontaneous ventilation will take place more gradually, enabling the patient to adapt better to spontaneous ventilation.

Figure 6:
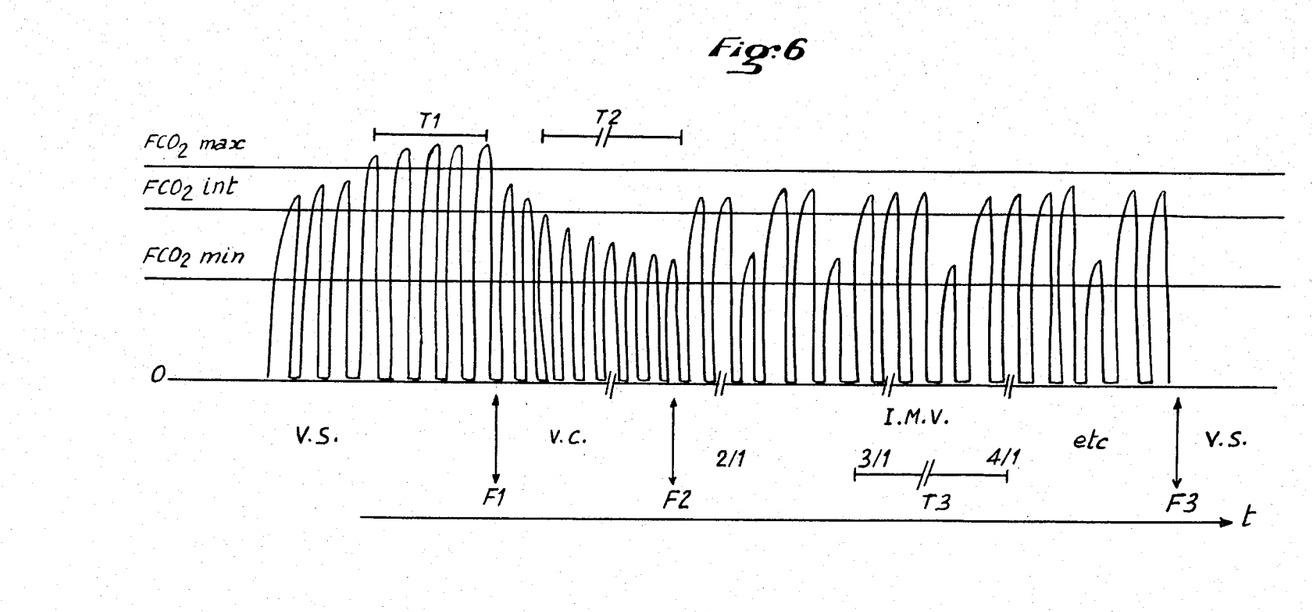
FIG. 6 is a representation of the output signal of the capnograph during a gradual withdrawal sequence, with changeover to the intermittent ventilation mode (IMV).

FIG. 6 shows a period of gradual withdrawal, with changeover to the IMV mode: intermittent forced ventilation. There is spontaneous ventilation up to the end F1 of T1, controlled ventilation up to the end F2 of T2, then IMV ventilation up to F3 and then spontaneous ventilation.

If $FCO_2max$ is exceeded in the IMV mode for a duration longer than T1, the controlled mode is engaged and the procedure begins again.

The time T3, which is the duration of each of the IMV types (2/1, 3/1, 4/1, and so on), can be fixed, in which case it is of the order of 3 minutes, or can vary, in which case it is adjustable by the doctor to suit each patient.

The use of a microprocessor can also make it possible to take account of the ventilation frequency in the spontaneous mode; if a maximum and minimum threshold is exceeded, this causes the respirator to start up in the controlled mode. This consideration of the ventilation frequency is a possible improvement to the system.

We claim:

1. Process for controlling the starting and stopping of an artificial respirator on a patient assisted by the artificial respirator during a surgical intervention of the patient's respiration and for allowing the patient progressively to recover his capability to breath alone at the end of the surgical operation, characterised in that the starting and stopping of the respirator are controlled as a function of the $CO_2$ content measured at the end of each expiration, $FCO_{2ET}$, of the gas exhaled by the patient, such that the respirator is turned on when the $CO_2$ content measured at the end of each expiration is outside of predetermined upper and lower limits for a predetermined period of time to provide controlled ventilation for the patient, and turned off when the $CO_2$ content measured at the end of each expiration is within said limits to provide for spontaneous ventilation of the patient.

2. Process according to claim 1, characterised in that a maximum threshold $FCO_2max$ and a minimum threshold $FCO_2min$ of the $CO_2$ content of the gas exhaled by the patient are determined, and in that, while the patient is under spontaneous ventilation with $FCO_2min < FCO_{2ET} < FCO_2max$, he remains under spontaneous ventilation, and as soon as he exceeds the thresholds constantly for a duration longer than an arbitrarily chosen duration, the patient is placed under controlled ventilation by the respirator.

3. Process according to claim 2, characterised in that a third threshold $FCO_2int$ is determined, which is intermediate between the first two, and in that the controlled ventilation is stopped if $$FCO_2min < FCO_{2ET} < FCO_2int$$

for a chosen period of the order of 5 minutes.

4. Device for controlling the starting and stopping of an artificial respirator for a patient who had been completely assisted by the artificial respirator, and for helping the patient to recover natural respiration, comprising: an artificial respirator (1) with an inhalation line (3) and an exhalation line (4), a line common to both said inhalation and exhalation lines, a cell (6) for analysing the $CO_2$ content of the gas which passes through it, said cell being placed in said line common to inhalation and to exhalation, a control module (11), and a capnograph (8) coupled between the cell and the control module and converting the signals received from the cell in order to deliver converted signals to said control module, said control module (11) being coupled between the capnograph and the respirator and receiving these signals from the capnograph in order to control the starting and stopping of the respirator, the module being arranged so as to control the starting and stopping of the respirator as a function of the $CO_2$ content, measured at the end of each exhalation, of the gas exhaled, such that the respirator is turned on when the $CO_2$ content measured at the end of each expiration is outside of predetermined upper and lower limits for a predetermined period of time to provide controlled ventilation for the patient, and turned off when the $CO_2$ content measured at the end of each expiration is within said limits to provide for spontaneous ventilation of the patient.

5. Device according to claim 4, characterised in that the capnograph (8) applies to the module an electrical voltage proportional at all times to the $CO_2$ content of the gas inhaled or exhaled, and in that the module (11) includes three detectors D1, D2, D3, which are arranged in parallel and which are coupled to the output of the capnograph, the detectors being adjustable in terms of voltage so that they assume one or another state according to whether the applied voltage is above or below a set voltage, and a logic circuit means functioning such that, if $FCO_{2ET}$ denotes the maximum voltage delivered by the capnograph on each exhalation, for $$D2 < FCO_{2ET} < D1$$

the logic circuit means does not order the respirator to start up, but does order it to start up if $FCO_{2ET}$ goes outside the limits D2, D1 constantly for a chosen duration of the order of 15 seconds, and orders the respirator to stop if the condition $D2 < FCO_{2ET} < D3$ is satisfied for a chosen period of time of the order of a few minutes, for example 3 to 5 minutes.

6. Device according to claim 5, further comprising control flip-flip means (35,36), having two inputs, for controlling the starting or stopping of the respirator in response to a zero state at one of its inputs, and wherein the detectors D1, D2, D3 are bistable elements assuming the zero state when the applied voltage is above the set voltage and the one state when the applied voltage is below the set voltage, and further comprising time delays T1, T2 and T3, each detector D1, D2, D3 being connected directly to an associated time delay T1, T2, T3, respectively.

7. Device according to claim 6, further comprising flip-flops B1, B2 and B3, and wherein the time delay T1 is connected to the control flip-flop means (35,36) of the respirator via the flip-flop B3, the level of which is controlled by the two flip-flops B1, B2 in series, the level of B1 being controlled by D1 and D2 and the level of B2 being controlled by B1 and D2.

* * * * *